(12) United States Patent
Barberi et al.

(10) Patent No.: US 9,199,242 B2
(45) Date of Patent: Dec. 1, 2015

(54) HAZARDOUS WASTE SANITATION AND REMOVAL DEVICE, METHODS OF USE AND APPLICATIONS THEREOF

(75) Inventors: Steven J. Barberi, Mission Viejo, CA (US); Felix F. Jakobi, Long Beach, CA (US); James F. Bennett, La Mirada, CA (US); Leslie G. Webber, Norco, CA (US); Louis J. Barberi, Perris, CA (US); Tadeusz J. Radonski, Corona, CA (US); Paul B. Englram, Oak Park, IL (US); Keith W. Kilham, Riverside, CA (US)

(73) Assignee: Trinova Medical Waste Solutions, LLC, Manhattan Beach, CA (US)

( * ) Notice: Subject to any disclaimer, the term of this patent is extended or adjusted under 35 U.S.C. 154(b) by 0 days.

(21) Appl. No.: 12/985,615

(22) Filed: Jan. 6, 2011

(65) Prior Publication Data

US 2011/0290919 A1   Dec. 1, 2011

(51) Int. Cl.
*B02C 19/00* (2006.01)
*A61L 2/00* (2006.01)
*A61L 11/00* (2006.01)
*B09B 3/00* (2006.01)
*A61L 2/18* (2006.01)

(52) U.S. Cl.
CPC ............ *B02C 19/0075* (2013.01); *A61L 2/183* (2013.01); *A61L 2/186* (2013.01); *A61L 11/00* (2013.01); *B09B 3/00* (2013.01); *B09B 3/0075* (2013.01)

(58) Field of Classification Search
CPC ........ B02C 19/0075; A61L 11/00; B09B 3/00
USPC ............... 422/28; 241/25; 101.5; 34/398
See application file for complete search history.

(56) References Cited

U.S. PATENT DOCUMENTS

| | | | | |
|---|---|---|---|---|
| 3,386,668 | A | | 6/1968 | Shepherd |
| 3,589,276 | A | | 6/1971 | Swallert |
| 3,910,775 | A | * | 10/1975 | Jackman .................... 44/589 |
| 3,926,379 | A | | 12/1975 | Dryden |
| 4,269,364 | A | | 5/1981 | Moriconi |
| 4,898,107 | A | * | 2/1990 | Dickinson .................. 110/346 |
| 4,984,748 | A | | 1/1991 | Kimura |

(Continued)

FOREIGN PATENT DOCUMENTS

| DE | 3829380 | 3/1990 |
|---|---|---|
| DE | 4138939 | 6/1993 |

OTHER PUBLICATIONS www.caprius.com (Jul. 13, 2011).

(Continued)

*Primary Examiner* — Kevin Joyner
(74) *Attorney, Agent, or Firm* — Sandra P. Thompson; Slater Hersey

(57) ABSTRACT

Hazardous waste sanitation and removal devices, along with methods of sanitizing hazardous waste materials, are described that include: a) a unitary shredder system, b) a transport system, a pre-treatment system or a combination thereof, comprising a reciprocating operation system, c) a treatment system, d) a dewatering system, a desolutionizing system or a combination thereof, and e) a collection system for disposal. Dewatering processes are also disclosed that includes at least one collection of wastes, at least one screw press, at least one conveyor system that carries the at least one collection of wastes after interaction with the at least one screw press, and at least one filter system.

7 Claims, 17 Drawing Sheets

(56) References Cited

U.S. PATENT DOCUMENTS

| | | |
|---|---|---|
| 5,064,124 A | 11/1991 | Chang |
| 5,078,965 A | 1/1992 | Pearson |
| 5,116,574 A | 5/1992 | Pearson |
| 5,217,688 A | 6/1993 | VonLersner |
| 5,273,221 A | 12/1993 | McCarthy |
| 5,387,350 A | 2/1995 | Mason |
| 5,620,654 A | 4/1997 | Mosenson |
| 5,673,861 A | 10/1997 | Miller |
| 6,250,236 B1 * | 6/2001 | Feizollahi .................... 110/346 |
| 6,494,391 B2 | 12/2002 | Mosenson |
| 6,866,832 B2 | 3/2005 | Garwood |
| 7,207,507 B2 | 4/2007 | Aichinger |
| 7,360,730 B2 | 4/2008 | Brown |
| 7,534,392 B1 | 5/2009 | Kodis |
| 7,534,405 B1 | 5/2009 | Kodis |
| 7,550,111 B2 | 6/2009 | Klaptchuk |
| 7,568,644 B1 | 8/2009 | Kodis |
| 7,699,247 B2 | 4/2010 | Kodis |
| 7,748,654 B2 | 7/2010 | Brown |
| 7,776,262 B1 | 8/2010 | Kodis |
| 7,918,337 B2 | 4/2011 | Hitson |
| 7,926,749 B2 | 4/2011 | Santandrea |
| 7,931,878 B2 | 4/2011 | Kodis |
| 2008/0008635 A1 * | 1/2008 | Jakobi et al. .................. 422/291 |

OTHER PUBLICATIONS

Press Release: Caprius, Inc. Announces Approval and Closing of Merger (Apr. 21, 2011).

* cited by examiner

HAZARDOUS WASTE SANITATION AND REMOVAL DEVICE, METHODS OF USE AND APPLICATIONS THEREOF

Green Technology Program: This application should be granted special status in the Green Technology Pilot Program, because it is an application pertaining to environmental quality. In addition, the subject matter of this application materially enhances the quality of the environment by contributing to the restoration or maintenance of one of the basic life-sustaining natural elements and also materially contributes to greenhouse gas emission reduction.

FIELD OF THE SUBJECT MATTER

The field of the subject matter is a hazardous waste sanitation and removal device, along with applications and methods of using the device.

BACKGROUND

Hazardous wastes are not something new that businesses are dealing with; however, the number of different hazardous wastes combined with the volume of hazardous wastes continues to increase exponentially. This increase in hazardous wastes is especially prevalent in the medical profession where hospitals, clinics, medical schools, veterinary schools and hospitals and doctors' offices dispose of tons of biological and/or hazardous wastes each year. These wastes must either be bagged, sealed and transported offsite for disposal or treated onsite. If they are transported offsite, then the medical facility may be responsible if the wastes end up in the water system or in a landfill where the landfill is not adequately secured for runoff or trespassers.

There are a number of patent and patent applications that attempt to address these problems. For example, U.S. Pat. No. 4,178,239 issued to Lowther discloses a system of treating aqueous sewage that contains both biodegradable materials and non-biodegradable materials by a series of processing steps that includes ozone pretreatment, oxygenation treatment in the presence of aerobic or facultative anaerobic microorganisms and another ozone treatment. This treatment process is not only complicated, but also does not allow for the treatment of significant solids in the waste. In fact, all of the solids are skimmed or filtered off in order to leave the sludge for treatment. The process is similar in U.S. Pat. No. 7,384,555 issued to Yasui et al. where solids are removed from a sludge waste material before treatment.

U.S. Pat. No. 5,077,007 issued to Pearson discloses a batch treatment process and related apparatus for disinfection of infectious waste. According to Pearson, hazardous wastes are put through at least one shredder to significantly reduce the size of the waste material. This design is problematic, because it introduces several shredders to the processing line if the waste materials are larger than those which can be accommodated by the primary shredder. All hazardous wastes cannot be accommodated by one shredder, according to Pearson.

Another design shortcoming in Pearson is the fluidized bed reactor vessel with diffusers, such as fine bubble diffusers or stone diffusers, at the bottom of the vessel. These types of diffusers cannot generate the material turn over that is required to adequately agitate the waste material. For example, the waste material usually has a high volume of plastic that floats in the solution. This material will not be completely turned over and mixed with the solution to provide adequate contact with the solution. In addition, by pumping air thru the product, you force the sanitizing chemistry, which is in the fluid solution, out into the gas space above the fluid and this lowers the concentration in the fluid, reducing its sanitizing capacity. If the waste material has been shredded enough to be fine and have a large surface area, then it is likely that these diffusers are going to become clogged with the waste materials if the concentration of solid waste materials exceeds more than a few percent of the total solution.

The Pearson design contemplates that the waste material is primarily water or liquid waste and a smaller percentage of waste solids. In addition, Pearson discloses that water is included initially in the bed reactor before the hazardous wastes are added for processing. This design is problematic for several reasons. First, it will obviously lead to more down time for the apparatus if there are more solids in the waste material. Second, if the user/operator can control the waste material to keep the percentage of solids lower, then it is likely that it will take longer to process waste materials, since most hazardous medical wastes are solid materials.

U.S. Pat. No. 5,116,574 issued to Pearson discloses a continuous treatment process and related apparatus for disinfecting infectious waste materials, which is different from the '007 Pearson patent by the introduction of the concept of continuous treatment. The same problems exist in this patent, in that it introduces several shredders to the processing line if the waste materials are larger than those which can be accommodated by the primary shredder. All hazardous wastes cannot be accommodated by one shredder, according to Pearson. While the Pearson process is continuous, the design is such that the waste material is primarily water or liquid waste and a smaller percentage of waste solids. This design is problematic for several reasons. First, it will obviously lead to more down time for the apparatus if there are more solids in the waste material. Second, if the user/operator can control the waste material to keep the percentage of solids lower, then it is likely that it will take longer to process waste materials, since most hazardous medical wastes are solid materials.

U.S. Pat. No. 5,820,541 issued to Berlanga Barrera discloses a treatment method for sterilization of biological, solid, liquid, ferrous metallic, non-ferrous metallic, toxic and "dangerous" hospital waste material. Upon review of this process, there are still additional pre-treatment and treatment steps that add to the complexity of the process. For example, the original waste materials are milled to break them down into smaller pieces and then the milled material is rinsed and treated with water before being centrifuged. This process is designed to bathe the residues "and dissolving the blood, semisolid, purulents, human body parts, etc., so as to be in good condition to receive the treatment that, with the formulation of compressed air, ozone, carbon dioxide, these gasses being combined by an ozone generator apparatus." The treatment of the washed and centrifuged materials is then performed followed by another centrifuge. Each of the steps of the process is conducted in an aqueous environment, except for the milling step.

U.S. patent application Ser. Nos. 11/930795, 11/568352, 11/212009 and 11/190343 are commonly-owned by TriNova™ and are incorporated herein by reference in their entirety. These applications disclose a hospital waste treatment apparatus and process that advances the field of waste treatment, but is still inadequate for large loads of medical and other hazardous wastes. The shredder is designed to accommodate large loads; however, once the materials enter the processing system comprising the pump, they can easily clog the system resulting in operational shutdowns and failures. In addition, there is no description or ability to process various wastes in different batches, as may be required if some wastes are relatively easy to disinfect and some are not. Finally, the systems disclosed are not designed to accommodate different disinfectant systems, such as gas, gas/liquid mixtures and/or liquid mixtures.

It would be ideal if a hazardous waste sanitation and removal device and system could easily prepare any type of hazardous waste for sanitation and disinfection, while at the same time actively monitoring the effectiveness and rate of sanitation. In addition, it would be ideal to develop such a system that reduces buildup and solids fall-out in the system, can be batch or continuous, can segregate and actively sanitize difficult or complex waste materials, and can be used with a gas, liquid and/or liquid/gas system.

SUMMARY

Hazardous waste sanitation and removal devices are described that include: a) a unitary shredder system, b) a transport system, a pre-treatment system or a combination thereof, comprising a reciprocating operation system, c) a treatment system, d) a dewatering system, a desolutionizing system or a combination thereof, and e) a collection system for disposal.

Methods of sanitizing hazardous waste material are described and include: a) providing a unitary shredder system, b) providing a transport system, a pre-treatment system or a combination thereof, comprising a reciprocating operation system, c) providing a treatment system, d) providing a dewatering system, a desolutionizing system or a combination thereof, e) providing a collection system for disposal, f) providing a hazardous waste material, g) introducing the hazardous waste material into the shredder system to produce a shredded waste material, h) transporting the shredded waste material to the treatment system utilizing the transport system, the pre-treatment system or a combination thereof, wherein the treatment system, the pre-treatment system or the combination thereof comprises a reciprocating operation system, i) treating the shredded waste material to produce a shredded treated material, j) dewatering or desolutionizing the shredded treated material, and k) collecting the shredded treated material in the collection system.

Dewatering processes are also disclosed that includes at least one collection of wastes, at least one screw press, at least one conveyor system that carries the at least one collection of wastes after interaction with the at least one screw press, and at least one filter system.

DETAILED DESCRIPTION

Surprisingly, a hazardous waste sanitation and removal device and system has been developed that addresses all of the goals and shortcomings that are outlined in the background section. Specifically, contemplated hazardous waste sanitation and removal devices and systems a) easily prepare any type of hazardous waste for sanitation and disinfection, b) actively monitor the effectiveness and rate of sanitation, c) reduce buildup and solids fall-out in the system, d) can be batch or continuous, e) can segregate and actively sanitize difficult or complex waste materials, f) can be used with a gas, liquid and/or liquid/gas system, g) can process hazardous wastes without any direct interaction from a user or operator, h) are mobile and easily located on site, i) does not require any specialized bags or liners and j) provide an integrated shredder system that cannot be bypassed.

Generally, contemplated devices and systems comprise five main areas for receiving and processing hazardous wastes: a) shredder system, b) transport and/or pre-treatment system, c) treatment system, d) dewatering and/or desolutionizing system, and e) collection for disposal. Each of the device and system areas comprises several unique features and steps not addressed by conventional systems and/or the prior art. For example, some of the prior art devices and systems required air or hydraulic pumps, along with inadequate tubing to transport a wet slurry of material and disinfectant to a dewatering system after spending some amount of time in a dwell area. This conventional pump and tubing combination can result in the need to significantly shred the waste materials, along with resulting downtime because of clogging in the tubing. In contemplated embodiments, the pump and tubing system are redesigned to eliminate the problems with conventional designs, in order to minimize clogging and device downtime. Also, the current device and process take advantage of gravity to move materials through the system, primarily because systems that push materials upward are inherently difficult to operate and maintain. In addition, dry shredded material may be sent directly to the treatment system without pretreatment. These distinct differences will be further discussed herein.

Figure 1:
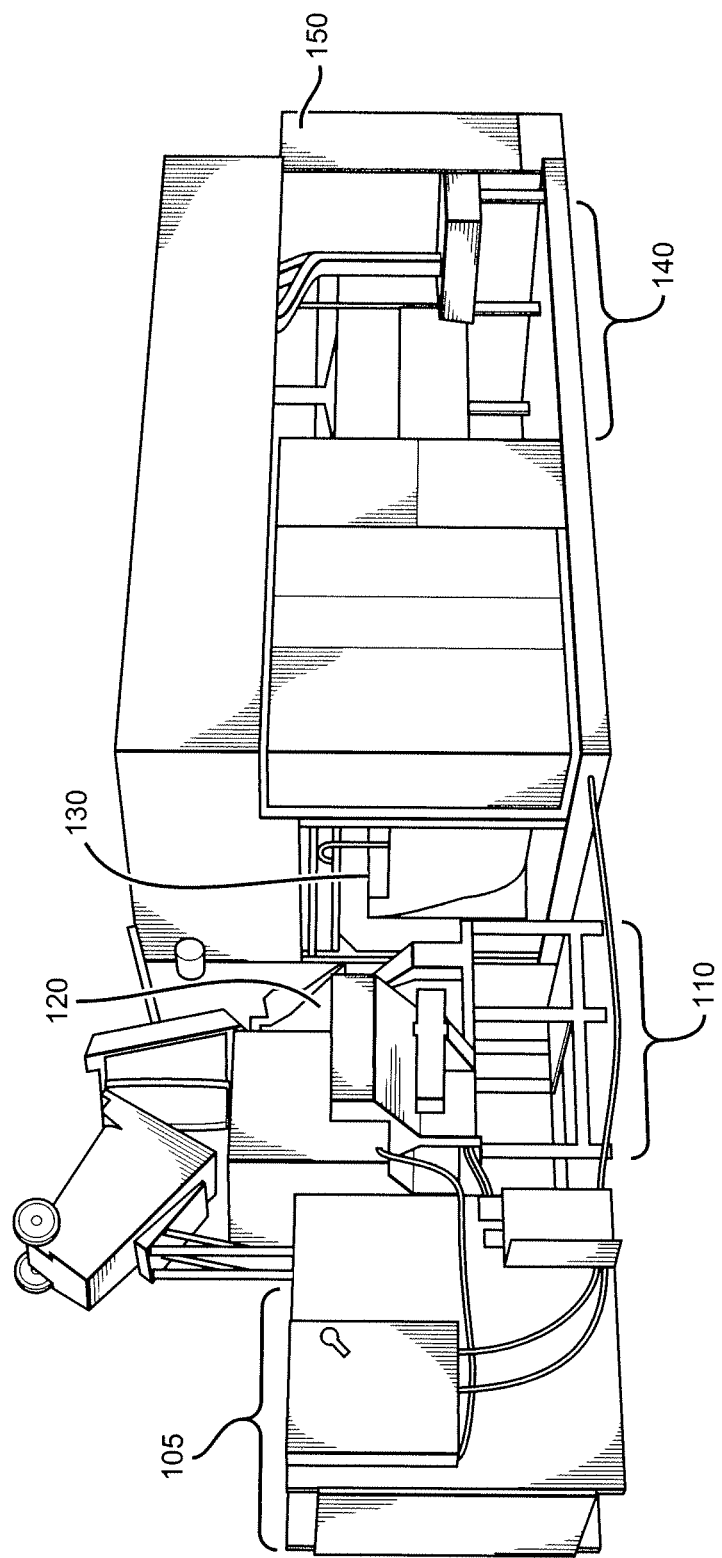
FIG. 1 shows a contemplated system.

Specifically, contemplated devices 100, as shown in FIG. 1, comprise: a) a unitary shredder system 110, b) a transport system, a pre-treatment system or a combination thereof comprising a reciprocating operation system 120, c) a treatment system 130, d) a dewatering system, a desolutionizing system or a combination thereof 140, and e) a collection system for disposal 150. In some contemplated embodiments, devices comprise a central control system. In other embodiments, a contemplated device comprises at least one monitoring system. In yet other embodiments, a contemplated central control system comprises the at least one monitoring system.

In order to show the significant flexibility of contemplated devices and processes, it is important to understand the scope of the hazardous wastes that can be sanitized and processed. Any and all wastes from a medical facility, hospital or clinic can be processed through a contemplated system. This scope isn't designed to say that only medical wastes can be processed, but is instead to show that any waste and hazardous waste can be processed in contemplated systems. For example, wastes that come from medical facilities include radioactive materials, fluorescent materials, biological materials, human waste materials, chemical materials, paper and plastic materials, metals, needles, glass, layered materials, fabrics and combinations thereof. As will be discussed further with respect to the shredder system, any and all of these materials can be appropriately and suitably broken down to transition through the sanitation and removal device.

Figure 2A:
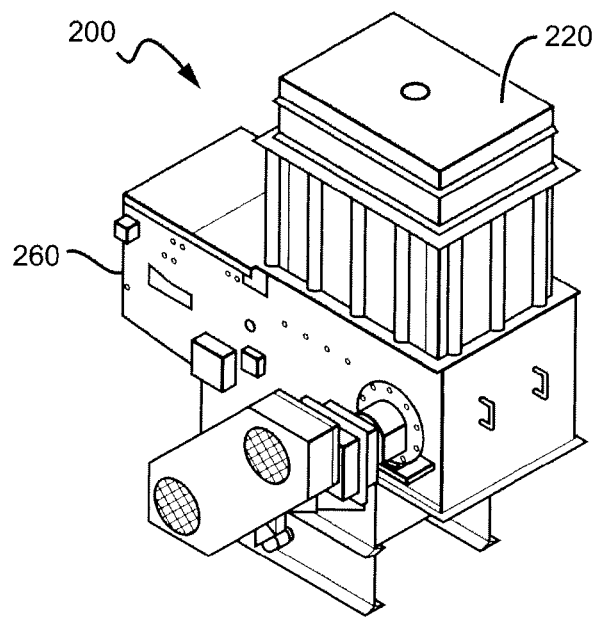
FIG. 2 shows a contemplated unitary shredder system.
Figure 2B:
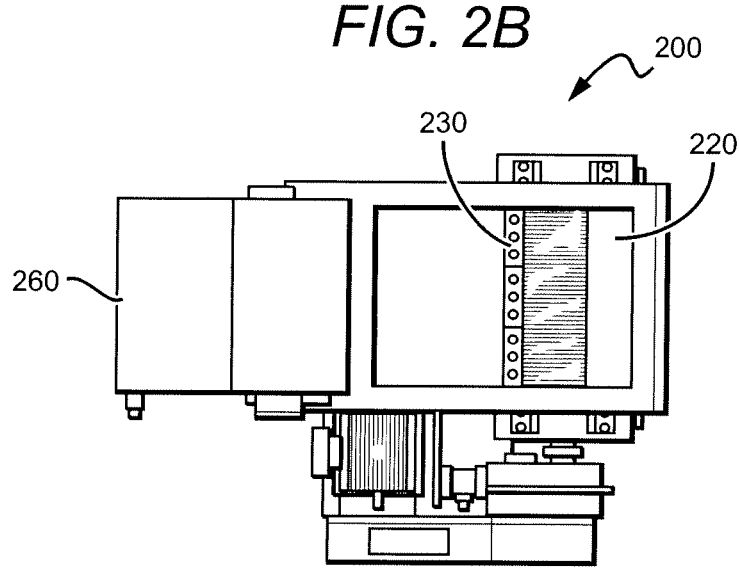
Figure 2C:
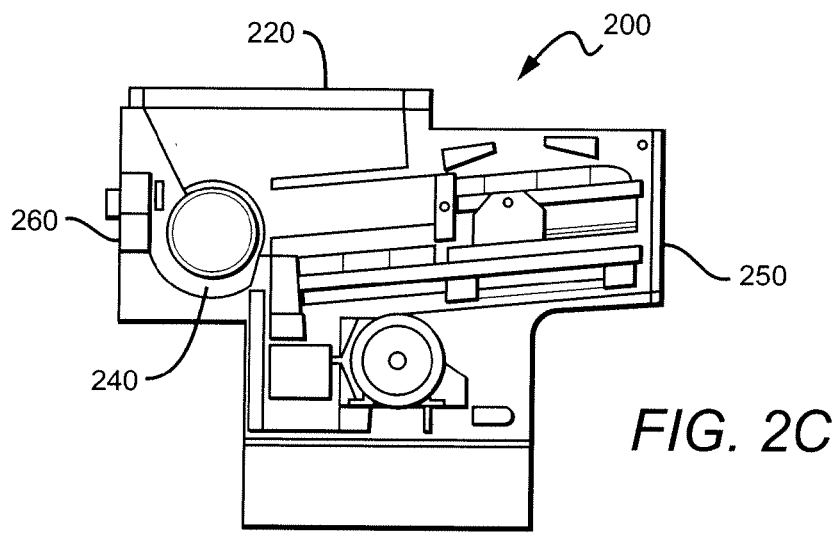

Contemplated devices comprise a unitary shredder system, which is shown in FIGS. 2A (side view 205), 2B (top view 210) and 2C (second side view 215). Part of the unitary shredder system is shown in FIG. 1 where the shredder system comprises a loader system 105 where waste materials are located near, introduced to or coupled with the unitary shredder system 110. The loader system 105 may comprise a lift cage and/or lifting mechanism that has some significant safety enhancements over conventional systems. For example, there are color sensors, radiation detectors and/or other methods of segregating wastes in order to prevent operators and workers from being exposed to harmful waste materials. As used herein, the term "unitary" with respect to the shredder system means that the shredder system is one unit and can accomplish all of the shredding necessary for the contemplated device in the one self-contained unit without the need for additional shredder steps or shredder systems, unlike other conventional technologies that include multiple shredder steps and machinery. Waste materials (not shown) are fed into the hopper 220 for a contemplated shredder system 200. One contemplated unitary shredder system shown in FIG. 2B shows the inside of the hopper 220. As waste materials enter the hopper 220, they come in contact with the shredder, which in this contemplated embodiment is a flat counterknife system 230. A triple cut screen 240, shown in FIG. 2C, may also be used in the shredder to provide additional shredding capacity. In this embodiment, there is a sliding floor 250 that directs waste materials into the shredder 240. After the waste is shredded, it is transported or sent to the outlet 260, which directs shredded waste into the transport system, the pre-treatment system or a combination thereof (not shown). Either at the direction of the user or when the hopper is full, the shredder system will operate functionally to shred the waste materials to a suitable size for processing in the sanitation system.

Contemplated devices comprise a transport system, a pre-treatment system or a combination thereof that acts as the transition point between the shredder system and the treatment system. It should be understood that the shredded waste materials may not need to be pretreated, and therefore, they will just transition or be transported to the treatment system. It should also be understood that if there is a pre-treatment stage, that it will not involve the pre-treating shredded waste materials traveling through a conventional tube and/or pipe with the aid of a basic air pump to the treatment area, as that process increases the likelihood that the system will clog or require downtime.

If the contemplated system has a pre-treatment stage, then the shredded waste will come in contact with a liquid pre-treatment component, a gaseous pre-treatment component or a combination thereof. A contemplated pre-treatment stage may result in the shredded waste materials being segregated in a vat or other suitable segregation container, such that the shredded waste materials can be pre-treated over a suitable time, at a suitable temperature and with a suitable pre-treatment component.

Contemplated treatment systems utilize a pump and pipe/tube arrangement that is novel for devices and systems of this kind. Contemplated pumps are designed for high solids and abrasive particle handling. This pump, unlike previous those utilized in conventional devices and systems, uses a reduced diameter pipe system, designed to maintain a high fluid velocity to carry the suspended solids, without settling and clogging. The solids are shredded to certain or prescribed particle size, and the contemplated pipe or tubing is large enough to transport these particles suspended in the fluid. A contemplated pump design also utilizes a high volume vacuum system that will violently or aggressively draw the slurry waste material into the pump. Compressed air pressure will then quickly discharge the slurry material into the batch tanks. This abrupt reciprocating operation keeps the heavy solid particles from falling out of the solution and clogging the system components. A contemplated liquid treatment component, gaseous treatment component, solid treatment component or a combination thereof is then pumped in the suction inlet as a jet, to further assist the prevention of deleterious build-up. It is contemplated that other types of pumps or transfer systems can be used to move this slurry to the batch tanks, as long as the reciprocating operation action is utilized in the device and/or system.

The shredded waste materials, as mentioned above, are then moved into the treatment system. At this point in the system, a central control system, at least one monitoring system or a combination thereof monitors, tests or otherwise can check the shredded waste to determine the level of hazardous contaminants. In these embodiments, if the level of contaminants does not exceed a certain pre-determined level, then the shredded waste materials enter the treatment system for at least one treatment stage. In some contemplated embodiments, additional treatment stages may be incorporated, as described below, to provide an increased or greater dosage of treatment components, which can also be called "super dosing". In some embodiments, the treatment system and constituent components may be adjusted so that disinfection reaches levels prescribed by the Environmental Protection Agency's Technical Assistance Manual: State Regulatory Oversight of Medical Waste Treatment Technologies.

This treatment system may comprise a continuous treatment feed, a batch treatment feed or a combination thereof. If the level of contaminants exceeds a certain pre-determined level, then the shredded wastes are segregated and moved into a batch processing system whereby the shredded waste materials may be pre-treated, additionally pre-treated or treated with different or stronger treatment components.

In one contemplated embodiment, the waste material slurry is pumped into the batch tank with a liquid treatment component to form a sanitizing solution. The strength of the sanitizing solution is measured and monitored, as it reacts with the contaminants in the medical waste. If the strength of the sanitizing solution is below the appropriate sanitizing level as monitored by the control system, additional liquid treatment component is added to the tank, until the appropriate concentration of sanitizing chemical is reached. Then this slurry is allowed to proceed to the dewatering station.

In every aspect of the treatment system, the central control system, the at least one monitoring system or the combination thereof monitors, tests or otherwise checks the shredded waste materials and/or the treatment components to ensure that the waste materials are sufficiently sanitized, disinfected or otherwise treated according to conventional or generally accepted treatment standards. The central control system, at least one monitoring system or combination thereof will then determine whether the temperature needs to be adjusted, the treatment time needs to be adjusted, the treatment components need to be adjusted, added or removed, material and/or whether the treatment system is complete. This process is also conducted for any and all waste materials that were segregated and processed for additional treatment.

Figure 3:
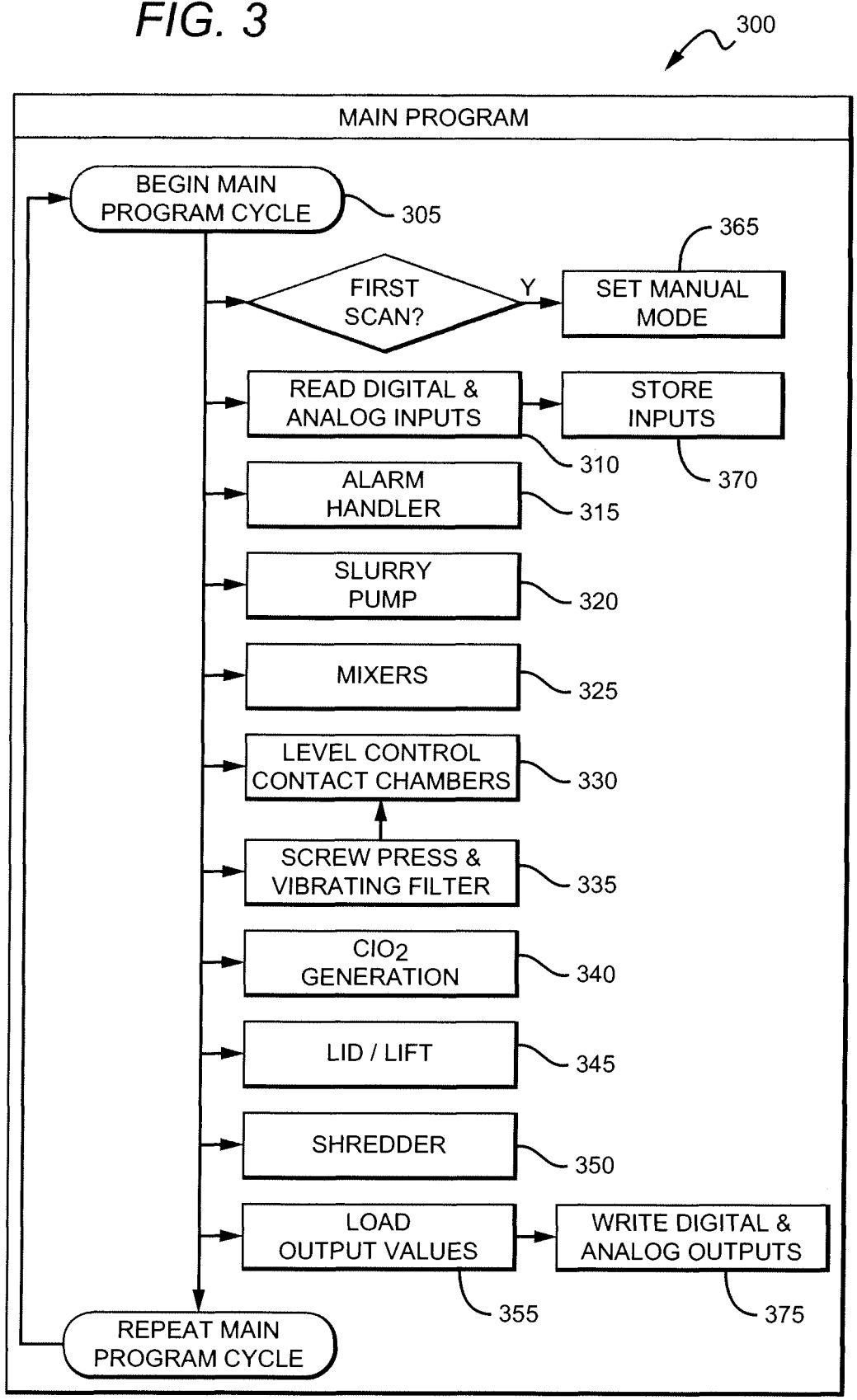
FIG. 3 shows an outline of a contemplated main program for a contemplated central control system and/or monitoring system.

In a contemplated embodiment, the central control system and/or monitoring system is novel and unique for this application. Specifically, FIG. 3 shows an outline of a contemplated main program 300 for a contemplated central control system and/or monitoring system. A contemplated main program comprises several components, such as those shown in FIG. 3, but it should be understood that there may be other components as needs arise. This contemplated main program 300 comprises a start step 305 where several components are reviewed, including reading digital and analog inputs 310, alarm handler or handlers 315, one or more slurry pumps 320, one or more mixer 325, one or more level control contact chambers 330, screw press and vibrating filters 335, chlorine dioxide or disinfectant generation 340, lid/lift mechanism 345 that is or is part of the loader system (not shown), unitary shredder 350, load output values 355 and if necessary, repeating the main program cycle 360. As part of this contemplated main program, the mode may be set in manual mode 365, inputs may be stored 370 and digital or analog outputs may be stored or written 375.

Figure 4:
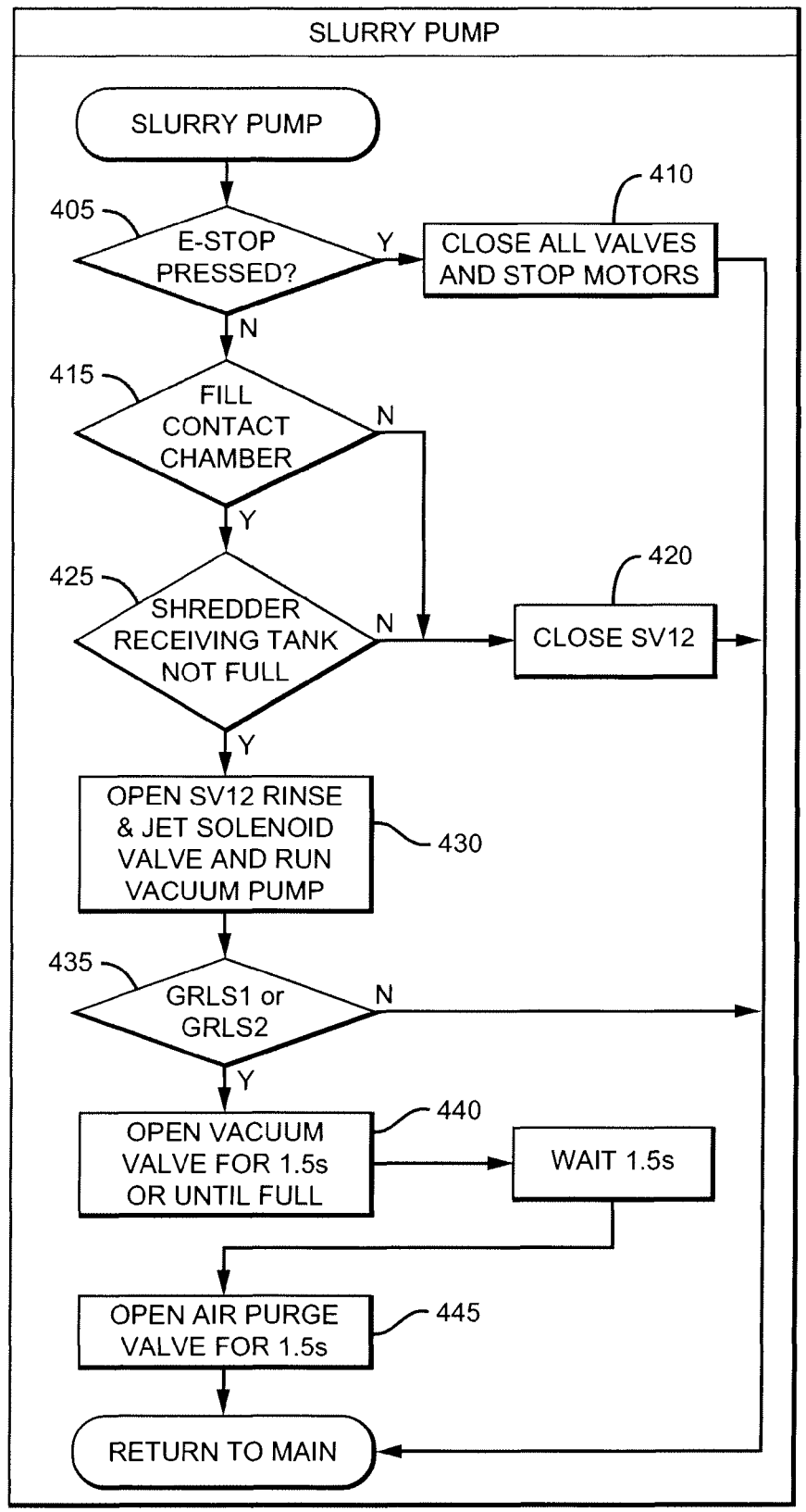
FIG. 4 shows a breakout of a slurry pump sub program for a contemplated central control system and/or monitoring system, such as the one shown in FIG. 3.

FIGS. 4-12 show breakouts of various components of a contemplated main program for a contemplated central control system and/or monitoring system, such as the one shown in FIG. 3. FIG. 4 shows a subroutine for the slurry pump program 400. The program first checks to see if the E-Stop safety mechanism has been pressed 405 and if so, all valves are closed and motors stopped 410. If not, then the contact chamber is checked 415 to see if it needs to be filled. If not, then SV12 is closed 420 and the program ends. If yes, then the shredder receiving tank needs to be filled 425. A rinse 430 of SV12 is opened and the vacuum pump is run—435, 440 and 445. Then the system returns to the main system program 300.

Figures 1, 5:
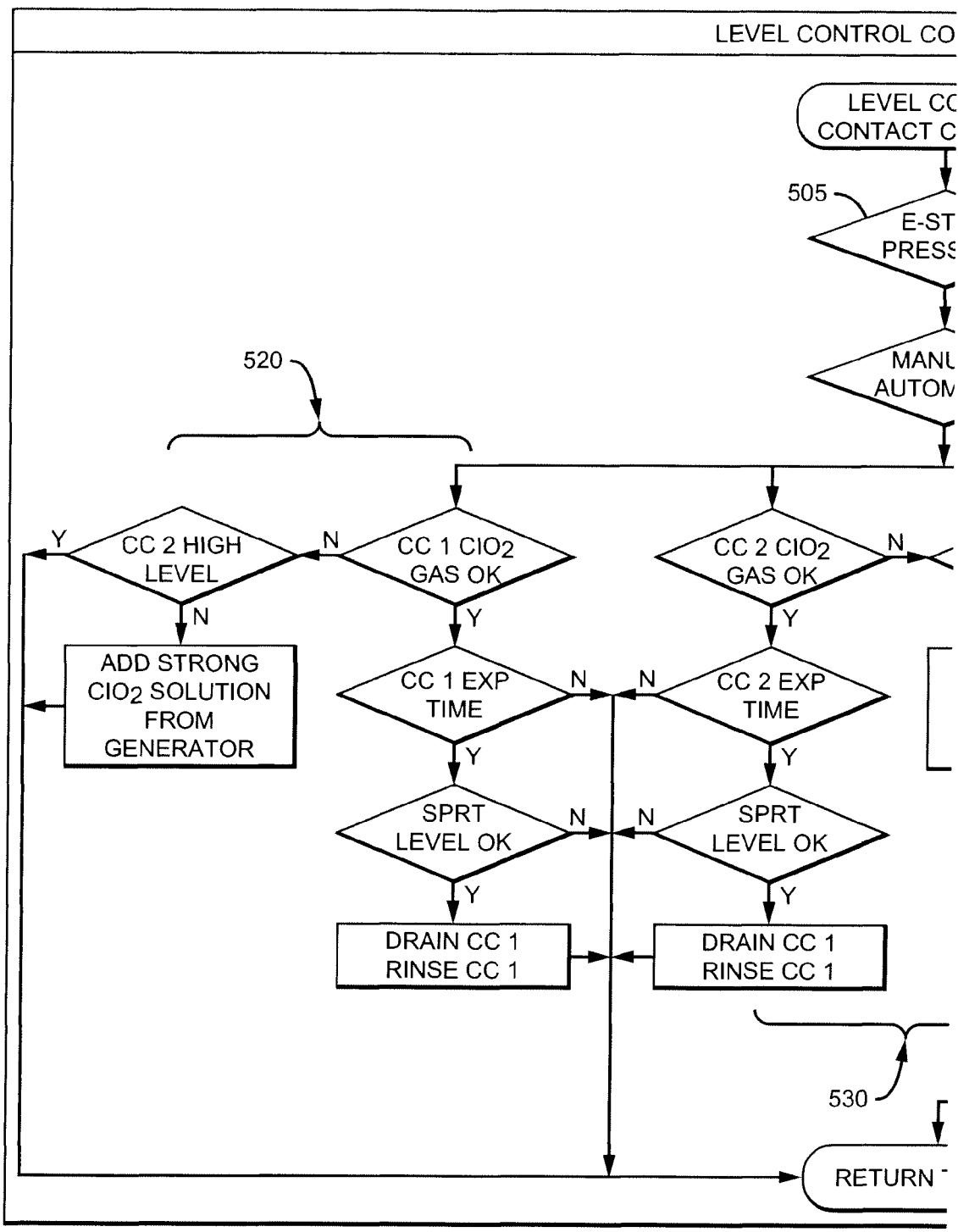
FIG. 5 shows a breakout of a level control contact chamber sub program for a contemplated central control system and/or monitoring system, such as the one shown in FIG. 3.
Figures 2, 5:
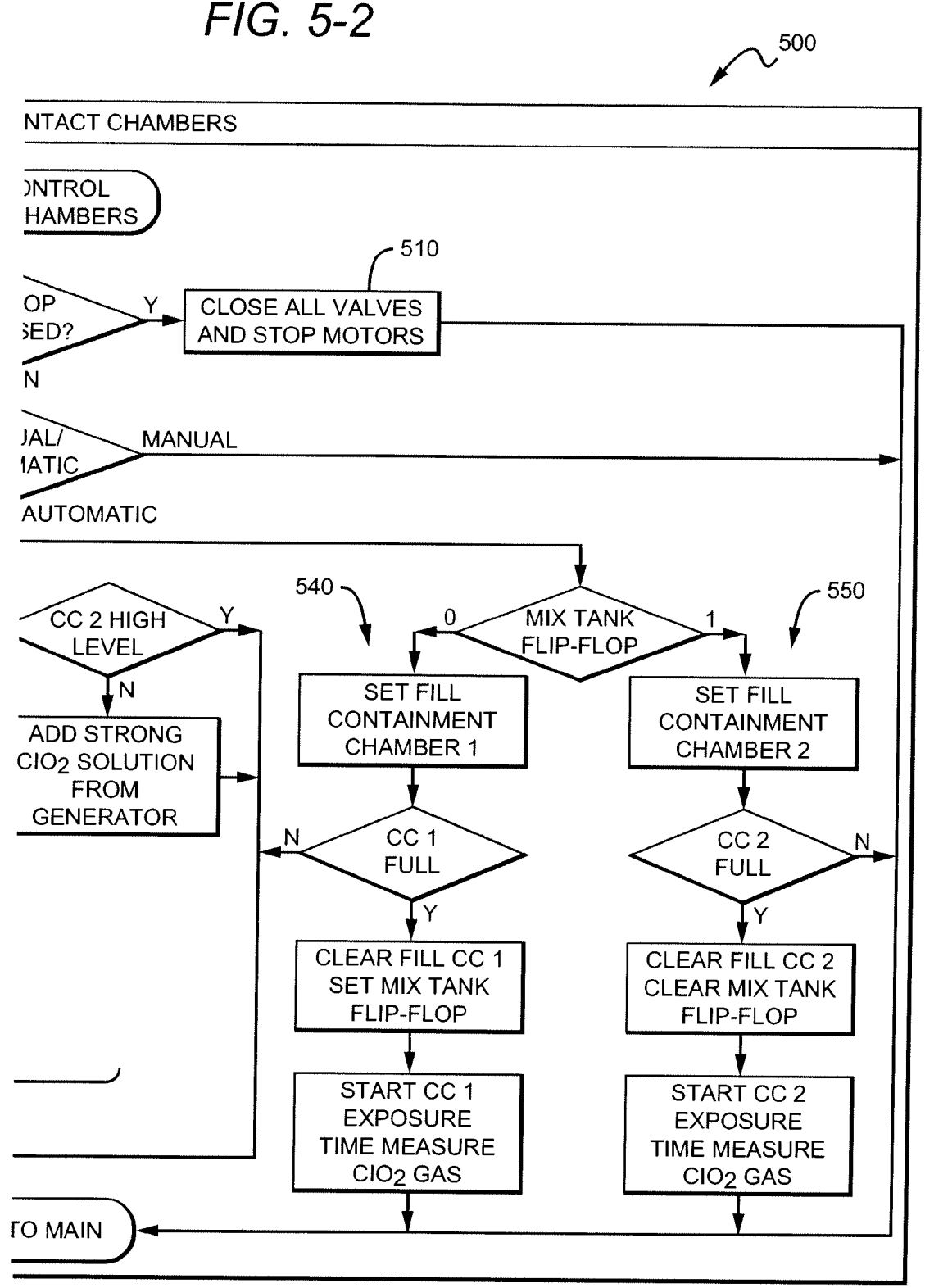

FIG. 5 shows a subroutine for the level control contact chambers 500. The program first checks to see if the E-Stop safety mechanism has been pressed 505 and if so, all valves are closed and motors stopped 510. If not, then the contact chambers are checked, drained and rinsed (steps 520 and 530). Chambers 1 and 2 are also filled and exposure time measured in this subroutine (steps 540 and 550). Once everything is finished, the subroutine reverts back to the main system program 300.

Figure 6:
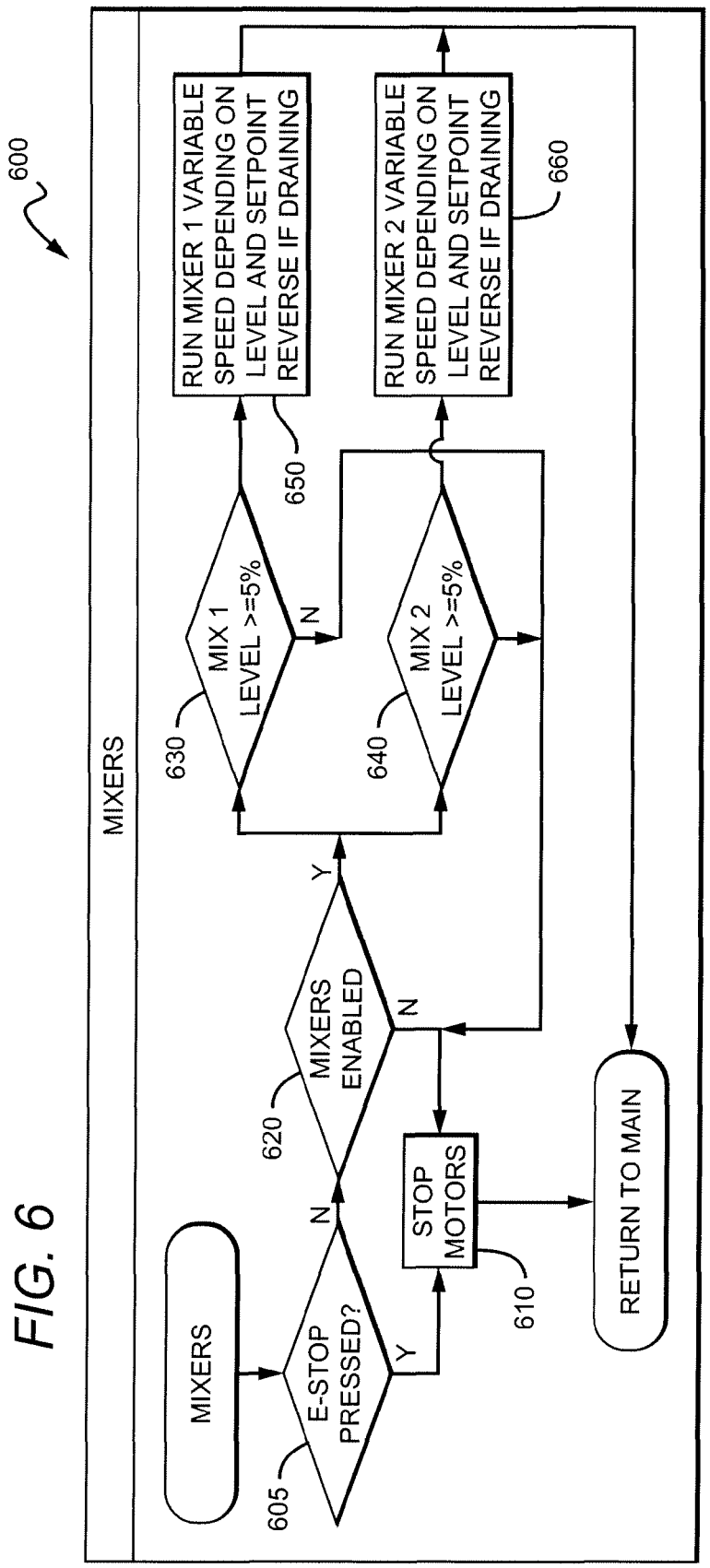
FIG. 6 shows a breakout of a mixer sub program for a contemplated central control system and/or monitoring system, such as the one shown in FIG. 3.

FIG. 6 shows a subroutine for the mixers 600. The program first checks to see if the E-Stop safety mechanism has been pressed 605 and if so, all valves are closed and motors stopped 610. If the subroutine moves forward, the mixers will be enabled 620 and the mix levels set 630 and 640. The mixers are run at variable speeds depending on the level and setpoint reverse if draining 650 and 660. Once everything is finished, the subroutine reverts back to the main system program 300.

Figure 7:
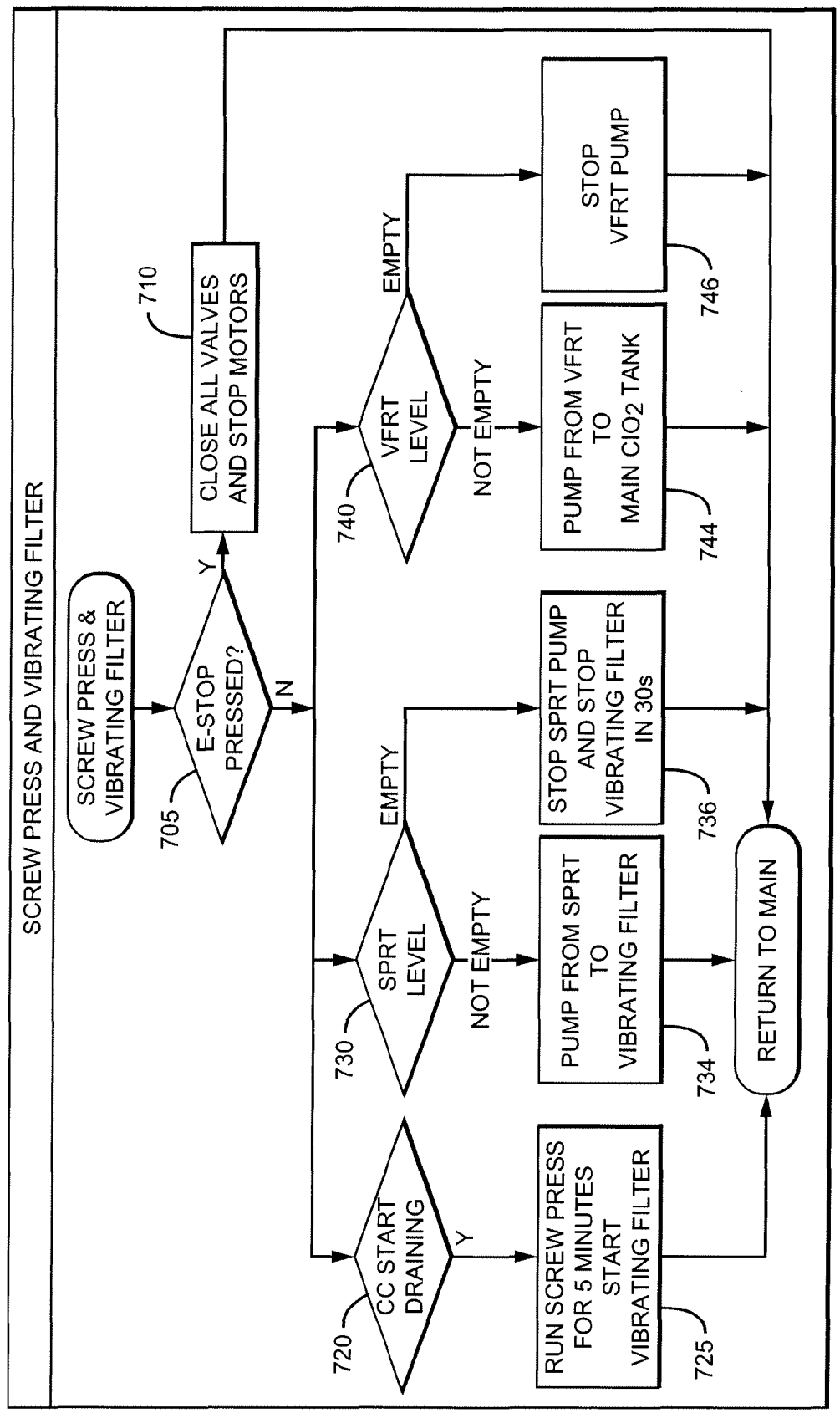
FIG. 7 shows a breakout of a screw press and vibrating filter sub program for a contemplated central control system and/or monitoring system, such as the one shown in FIG. 3.

FIG. 7 shows a subroutine for the screw press and vibrating filter 700. The program first checks to see if the E-Stop safety mechanism has been pressed 705 and if so, all valves are closed and motors stopped 710. If the program moves forward, the chamber(s) start draining 720, the SPRT level is checked 730 and the VFRT level is checked 740. After these modules are checked, the screw press and vibrating filters begin to work and then stop (725, 734, 736, 744, 746). Once everything is finished, the subroutine reverts back to the main system program 300.

Figure 8:
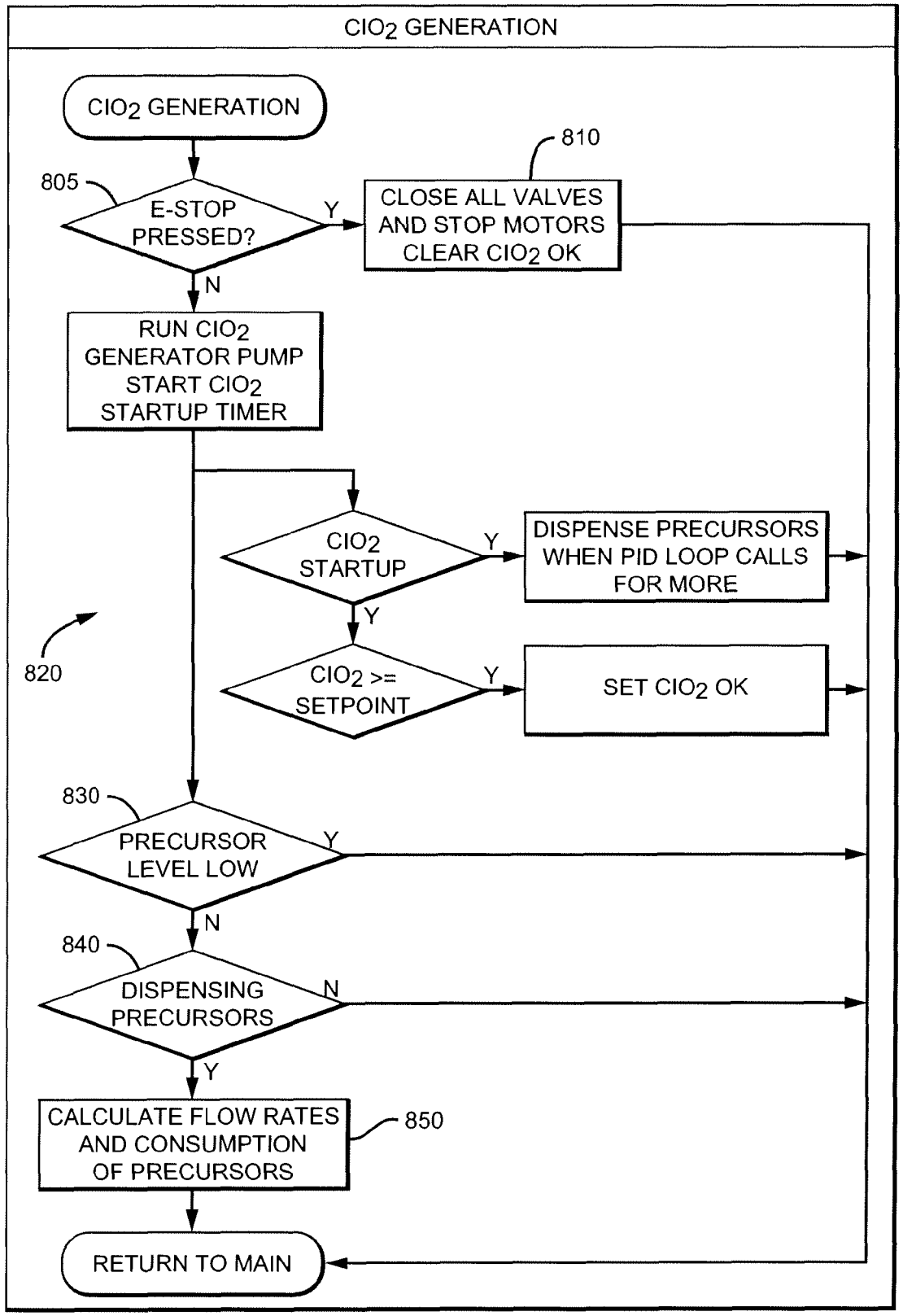
FIG. 8 shows a breakout of a chlorine dioxide generation sub program for a contemplated central control system and/or monitoring system, such as the one shown in FIG. 3.

FIG. 8 shows a subroutine for the chlorine dioxide and/or disinfectant generation system 800. The program first checks to see if the E-Stop safety mechanism has been pressed 805 and if so, all valves are closed and motors stopped 810. If the program moves forward, the chlorine dioxide and/or disinfectant generation system is started 820, precursors or constituents checked 830, dispensed 840 and flow rates calculated 850. Once everything is finished, the subroutine reverts back to the main system program 300.

Figure 9:
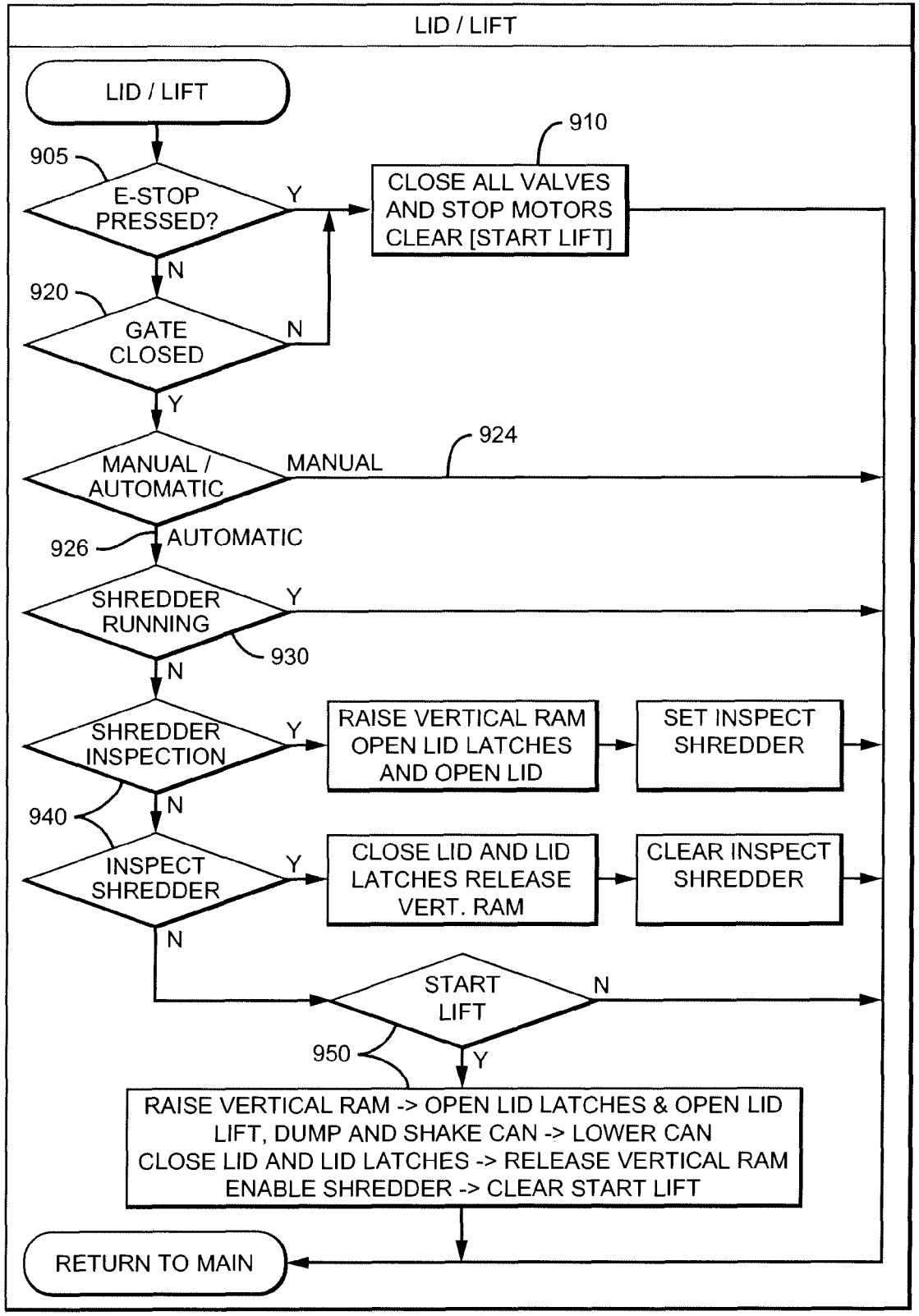
FIG. 9 shows a breakout of a lid/lift sub program for a contemplated central control system and/or monitoring system, such as the one shown in FIG. 3.

FIG. 9 shows a subroutine for the lid/lift mechanism system 900 that feeds waste materials into the unitary shredder system (not shown). The program first checks to see if the E-Stop safety mechanism has been pressed 905 and if so, all valves are closed and motors stopped 910. If the program moves forward, the gate is closed 920 and the system is put on either manual 924 or automatic 926 run mode. If it is in automatic run mode 926, the shredder starts running 930, it is inspected 940 and the lift mechanism 950 is started. Once everything is finished, the subroutine reverts back to the main system program 300.

Figure 10:
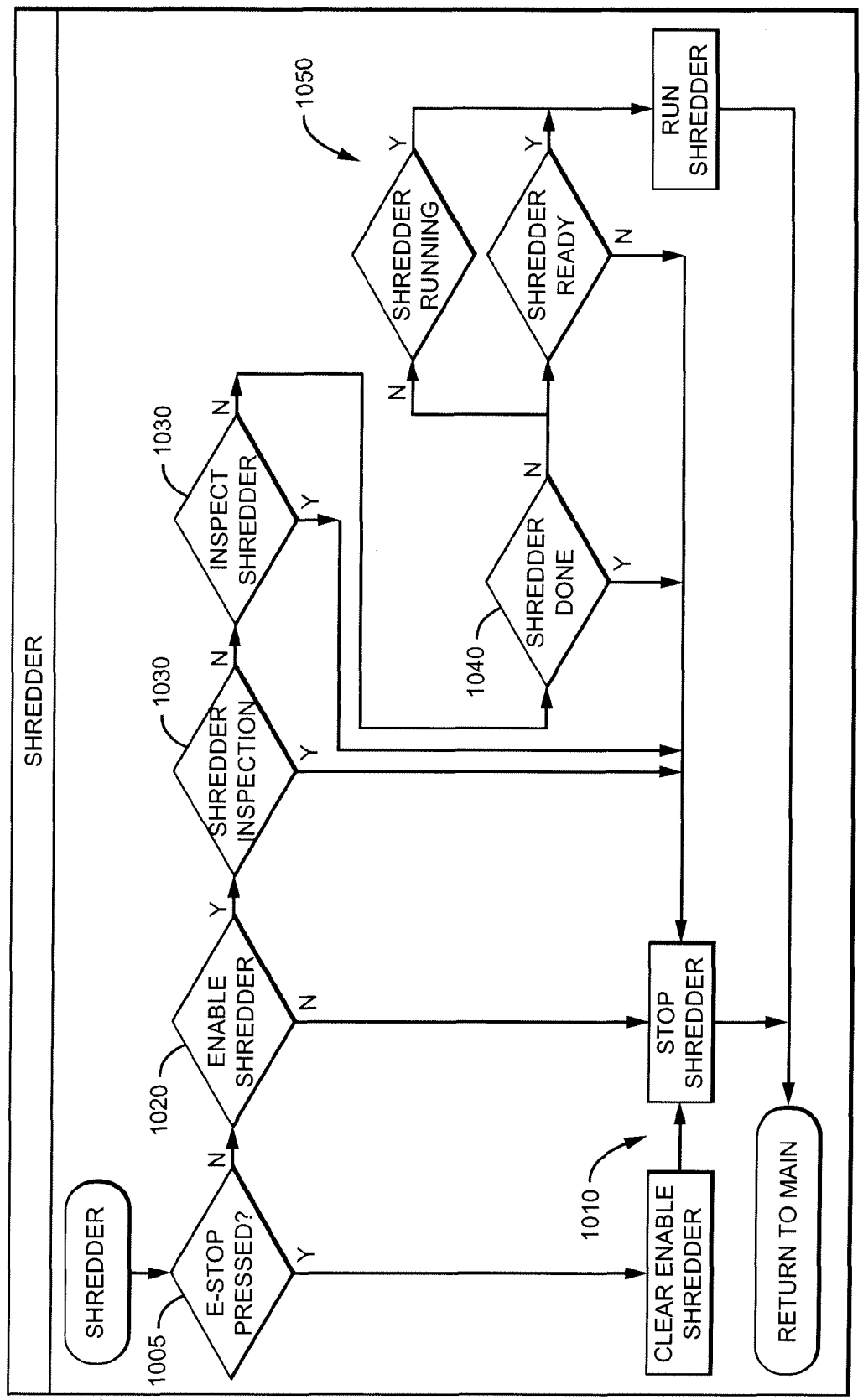
FIG. 10 shows a breakout of a shredder sub program for a contemplated central control system and/or monitoring system, such as the one shown in FIG. 3.

FIG. 10 shows a subroutine for the shredder system 1000. The program first checks to see if the E-Stop safety mechanism has been pressed 1005, and if so, all valves are closed and motors stopped 1010. If the program moves forward, the shredder is enabled 1020, inspected 1030, stopped 1040 and completed 1050. Once everything is finished, the subroutine reverts back to the main system program 300.

Figures 1, 11:
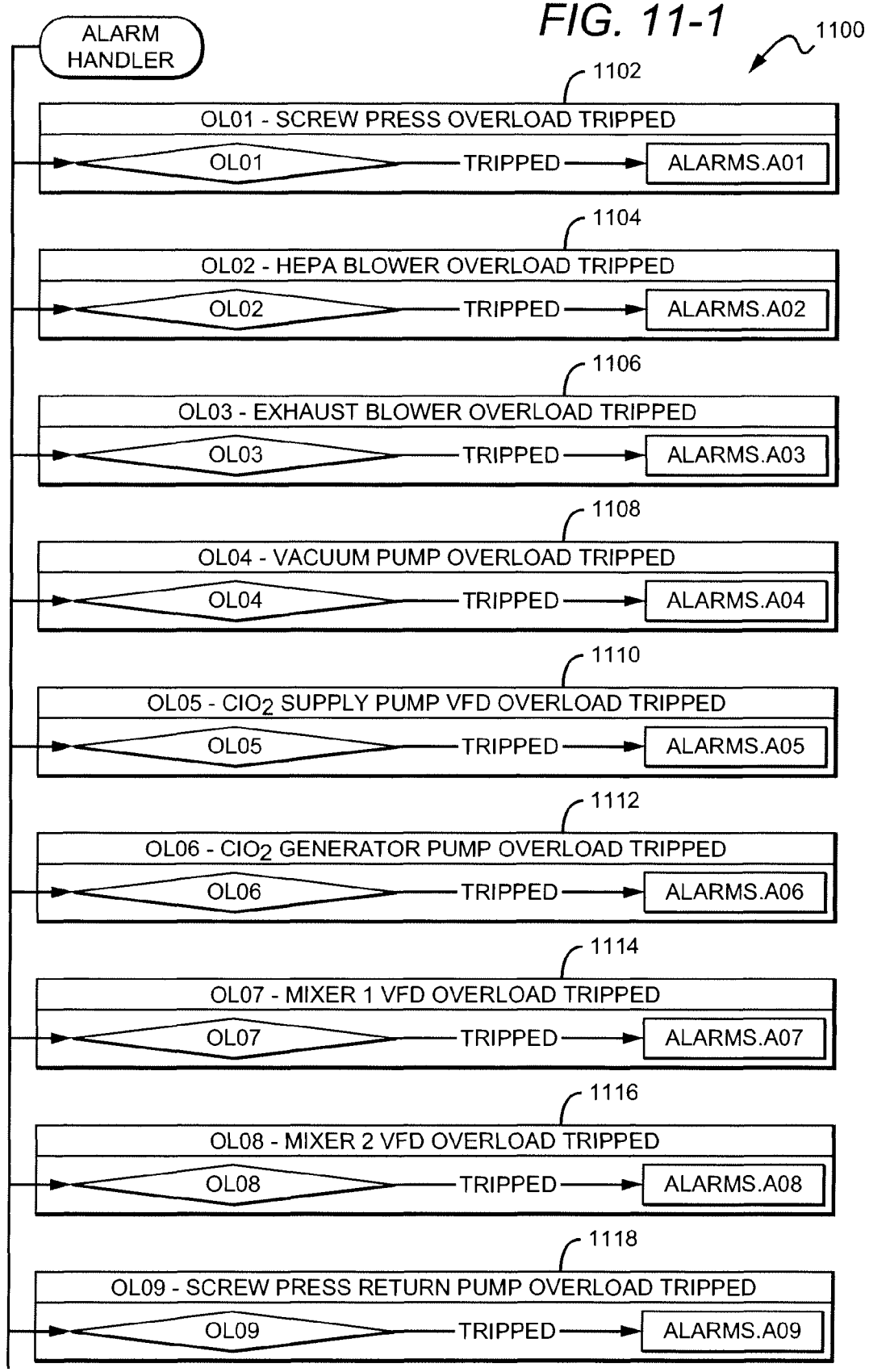
FIG. 11 shows a breakout of an alarm handler sub program for a contemplated central control system and/or monitoring system, such as the one shown in FIG. 3.
Figures 2, 11:
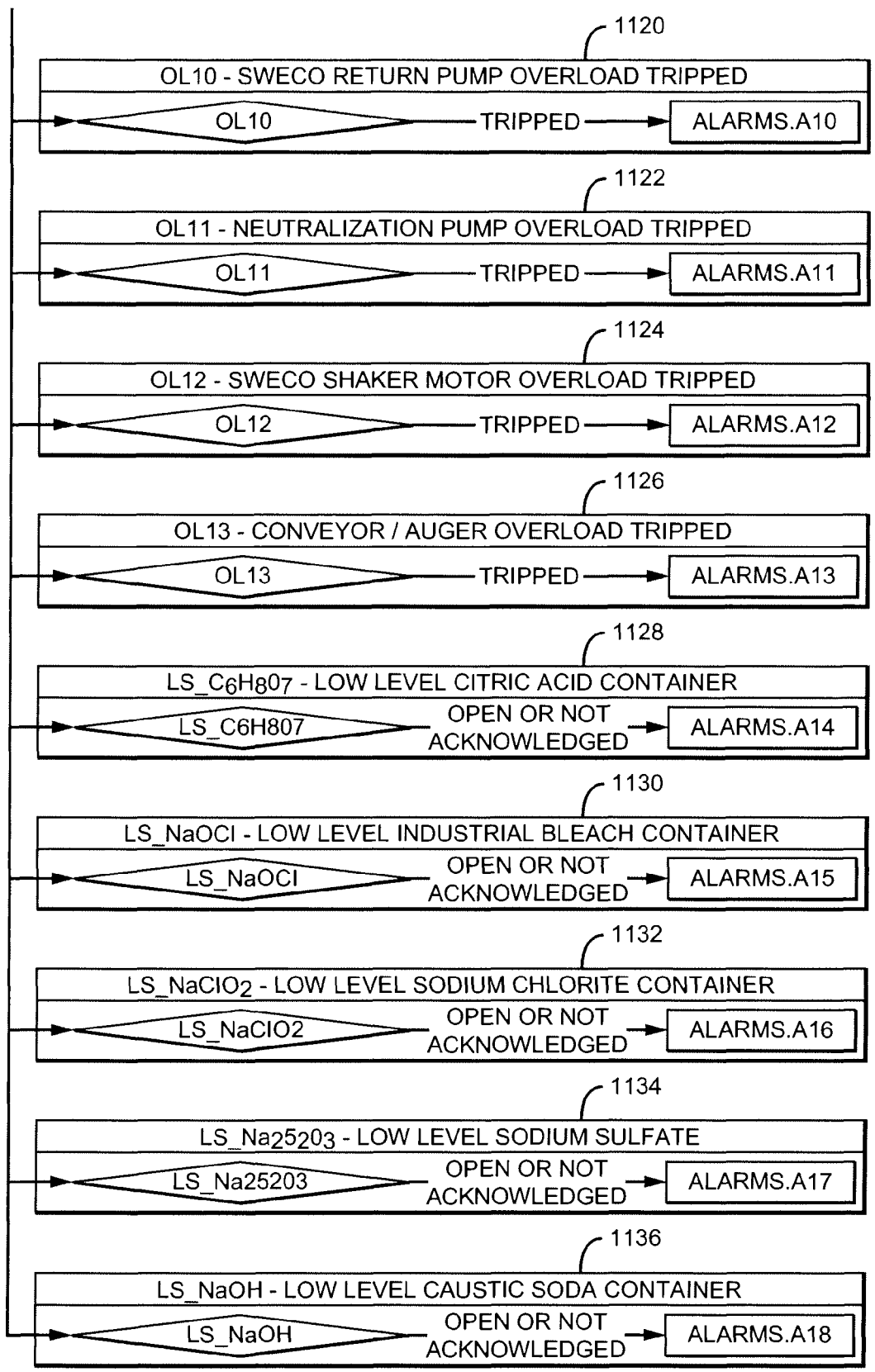
Figures 1, 12:
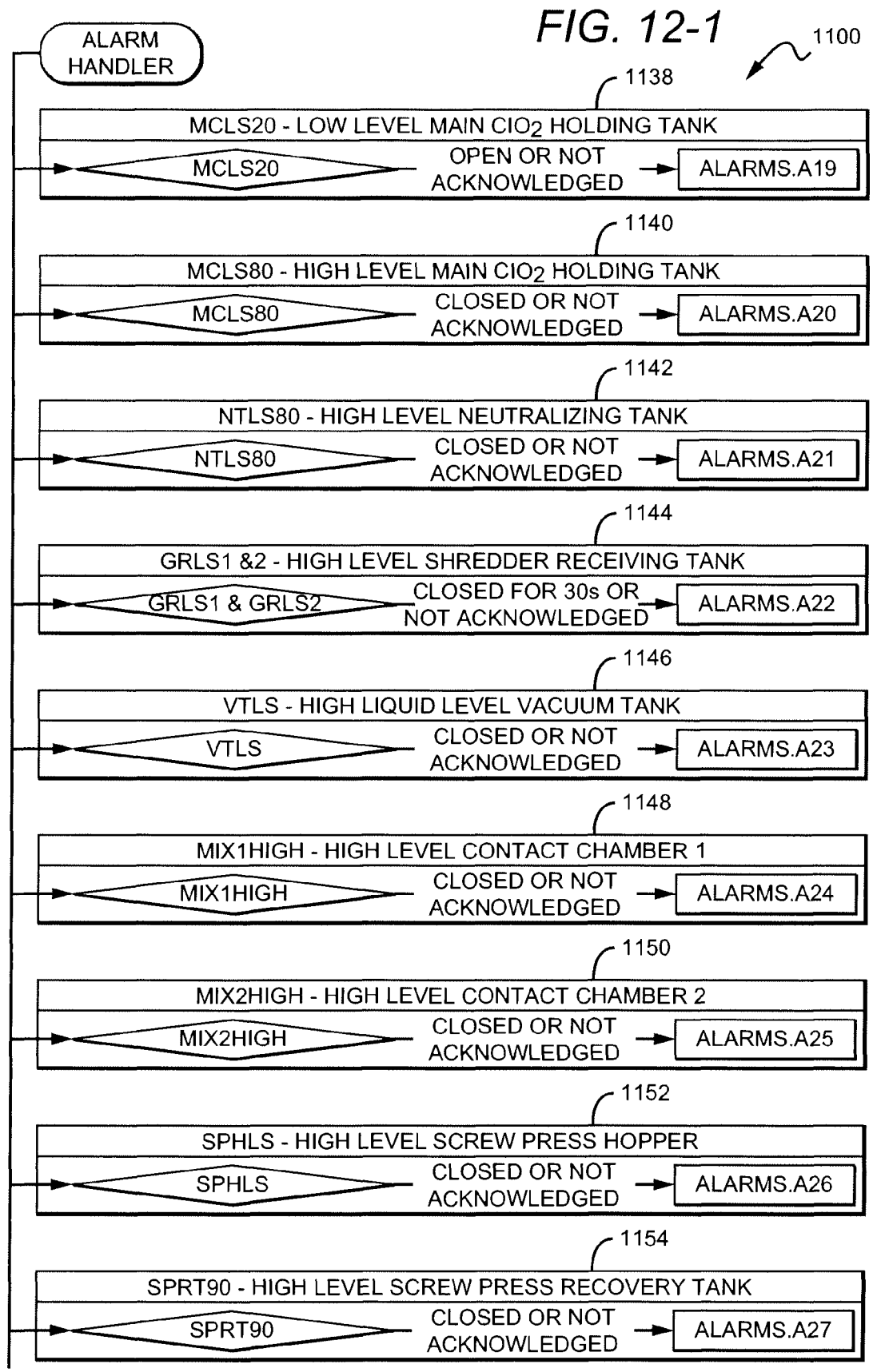
FIG. 12 shows a breakout of an alarm handler sub program for a contemplated central control system and/or monitoring system, such as the one shown in FIG. 3.
Figures 2, 12:
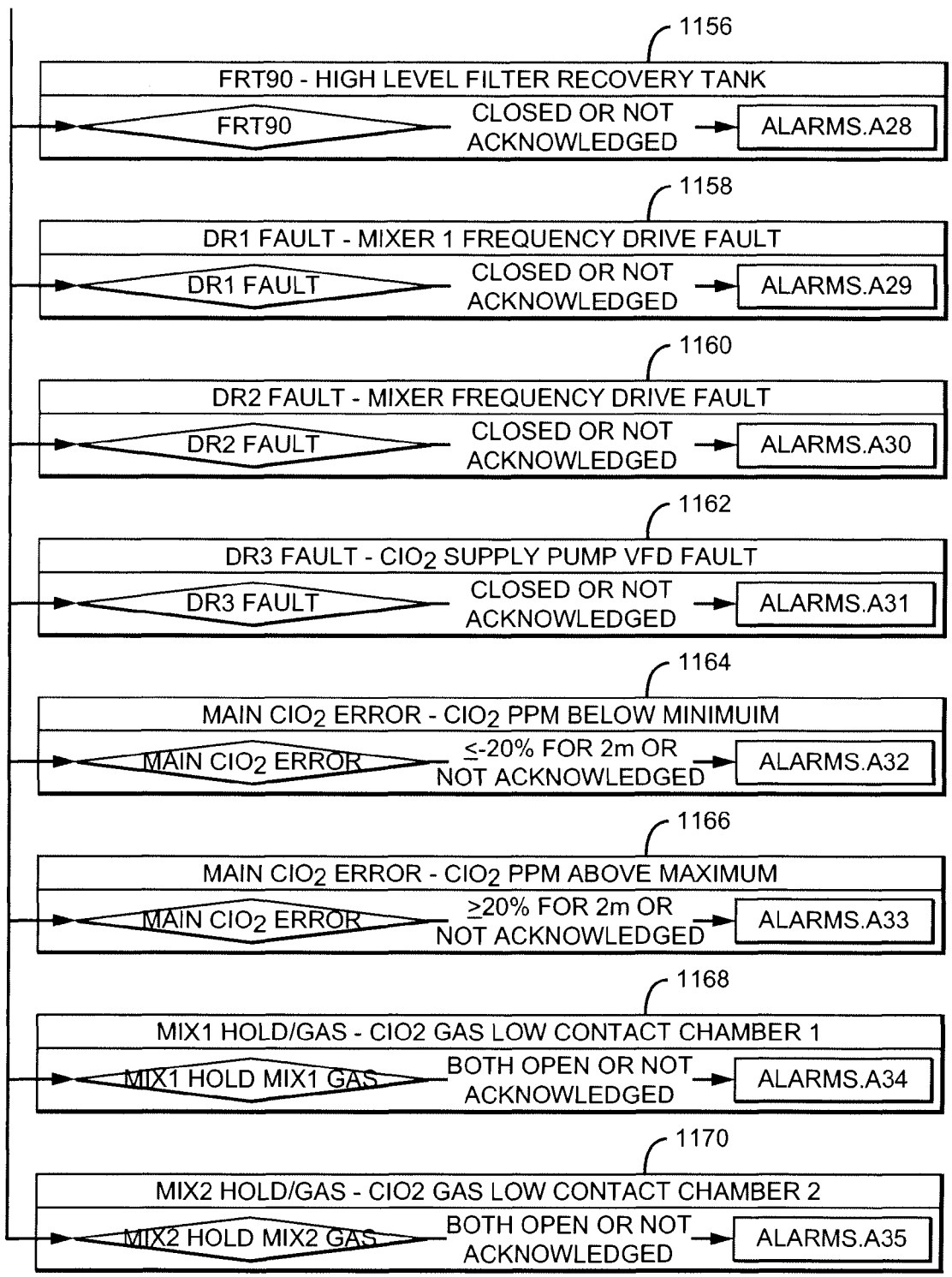

FIGS. 11 and 12 show the subroutine for the alarm system 1100. As each of these individual alarms are tripped an alarm is generated in the main program 300 and transmitted to the user/operator. Some contemplated alarms are shown and are as follows: Screw press overload tripped 1102, Hepa blower overload tripped 1104, Exhaust blower overload tripped 1106, Vacuum pump overload tripped 1108, Chlorine dioxide supply pump VFD overload tripped 1110, Chlorine dioxide generator pump overload tripped 1112, Mixer 1 VFD overload tripped 1114, Mixer 2 VFD overload tripped 1116, Screw press return pump overload tripped 1118, Sweco return pump overload tripped 1120, Neutralization pump overload tripped 1122, Sweco shaker motor overload tripped 1124, Conveyor/Augers overload tripped 1126, Low level citric acid container 1128, Low level industrial bleach container 1130, Low level sodium chlorite container 1132, Low level sodium sulfate 1134, Low level caustic soda container 1136, Low level main chlorine dioxide holding tank 1138, High level main chlorine dioxide holding tank 1140, High level neutralizing tank 1142, High level shredder receiving tank 1144, High liquid level vacuum tank 1146, High level contact chamber 1 1148, High level contact chamber 2 1150, High level screw press hopper 1152, High level screw press recovery tank 1154, High level filter recovery tank 1156, Mixer 1 frequency drive fault 1158, Mixer 2 frequency drive fault 1160, Chlorine dioxide supply pump VFD fault 1162, Chlorine dioxide PPM below minimum 1164, Chlorine dioxide PPM above maximum 1166, Chlorine dioxide gas low contact chamber 1 1168 and Chlorine dioxide gas low contact chamber 2 1170. As indicated above, there could be additional alerts developed and/or utilized as contemplated systems are modified and/or used.

As mentioned earlier, it should be understood that there are numerous variations of main and sub programs for contemplated central control systems and/or monitoring systems depending on the needs of the overall system.

As contemplated herein, liquid pre-treatment components, liquid treatment components, gaseous pre-treatment components, gaseous treatment components, solid pre-treatment components, solid treatment components or a combination thereof may comprise any suitable chemical, gas, liquid or solid that functions according to the needs of the system and process. These chemicals, gases, liquids or solids may be added to the system in their intended form or produced by the system. For example, if ozone is used as a pre-treatment or treatment component, ozone may be added by a tank or produced from a plasma or other electrical discharge. Contemplated solids may include those solid materials that chemically aid in disinfecting or sanitizing or may be those solids that act as catalysts or agitation agents for a solution or gas. Contemplated liquids and/or gases may include oxygen, nitrogen, one or more halogens, sulfur, hydrogen, boron or any other suitable element or combination of elements. Contemplated liquids and/or gases may comprise at least one acid, at least one base or a pH neutral component. In some embodiments, a contemplated liquid and/or gas comprises dioxides, oxides and/or ozone. In other embodiments, a contemplated liquid and/or gas comprises chlorine dioxide and/or ozone.

Once the shredded waste materials are sufficiently treated, they are transported either by gravity or a transport system to a dewatering system, a desolutionizing system or a combination thereof. This contemplated step in the process is designed to wash away any residual chemicals and dry the shredded treated materials. It is contemplated that the central control system, at least one monitoring system or combination thereof may implement one final check of the shredded materials to ensure that they are sufficiently treated. If not, then the waste materials may be transported or otherwise conveyed back to the treatment system for additional processing. The shredded treated materials are vibrated, rotated or otherwise disrupted to complete the drying process. An additional auger system may be used with a solids separator to eliminate excess water and lint from the dewatering process.

Once the shredded treated materials are processed and dry, they are considered ready for disposal. In some embodiments, the dewatering system, desolutionizing system or the combination thereof also functions as the disposal system, and in other embodiments, they are separate. In either embodiment, it is contemplated that the user or operator can remove the shredded treated materials and dispose of them in any conventional manner, such as a dumpster, bin or trashcan.

Figure 13A:
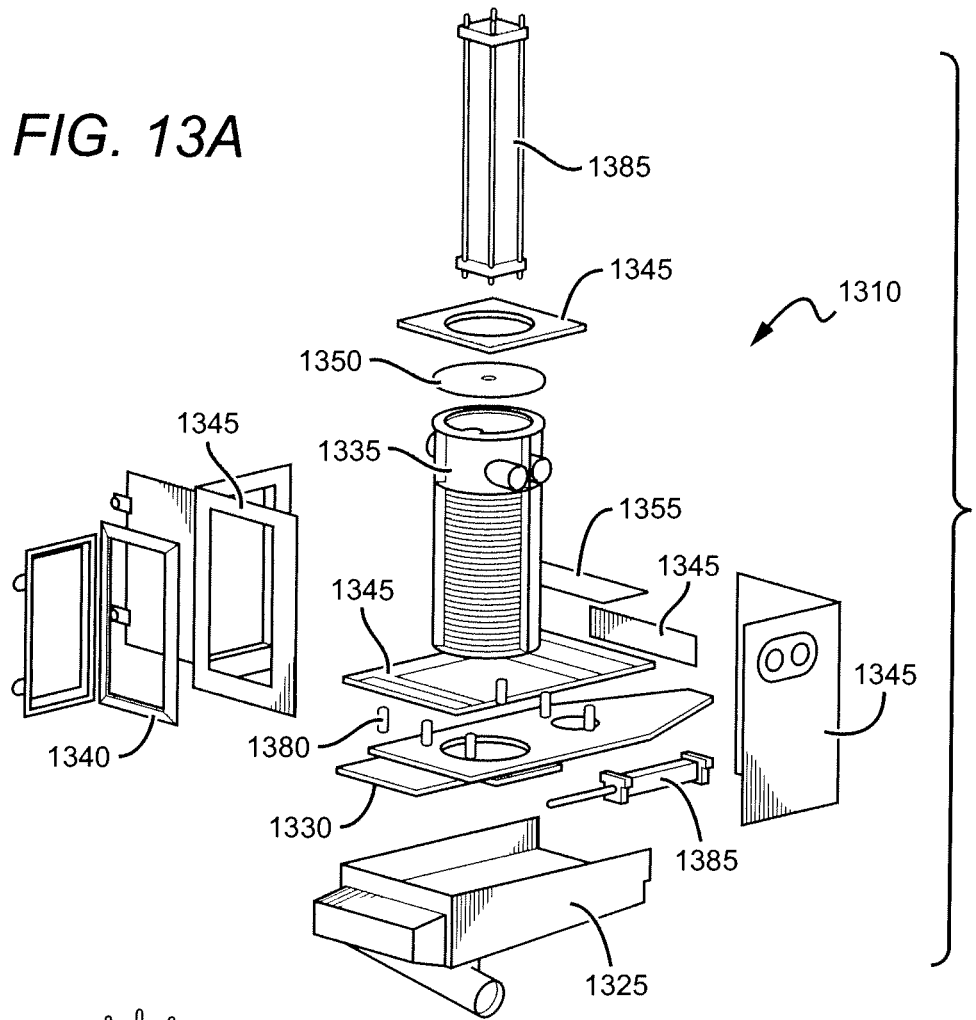
FIG. 13 shows a contemplated dewatering process.
Figure 13B:
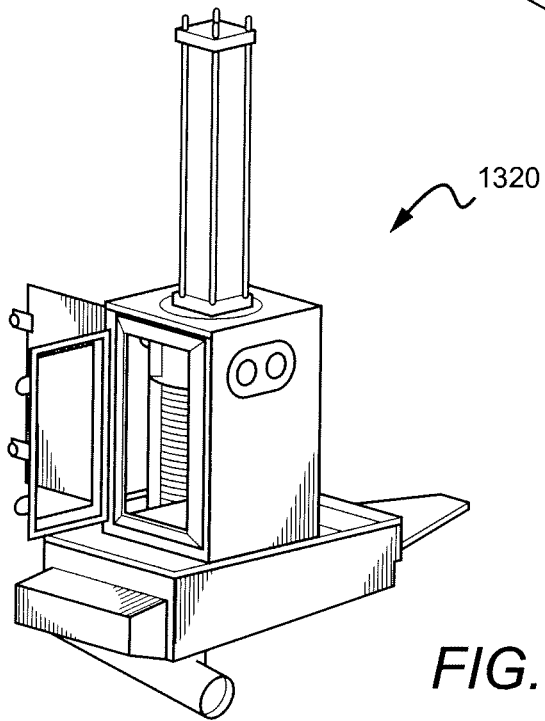

Dewatering processes, as shown in FIG. 13, are also disclosed that includes at least one collection of wastes, at least one screw press, at least one conveyor system that carries the at least one collection of wastes after interaction with the at least one screw press, and at least one filter system. In some embodiments, the collection of wastes comprises at least one shredded waste. In other embodiments, the collection of wastes comprises at least one shredded waste, at least one treated waste or a combination thereof. In some embodiments, the at least one filter system comprises a vibrating filter system. In other embodiments, the at least one screw press return tank, at least one vibrating filter return tank or a combination thereof. FIG. 13A shows an exploded view of a contemplated vertical dewatering press 1310. This contemplated vertical dewatering press comprises a sloped pan 1325, a main plate dewatering slide 1330, a dewatering screen assembly 1335, a door or hatch 1340, upper box panels 1345, a retaining cap 1350, an upper box patch 1355, a main plate spacer 1380 and air cylinders 1385. FIG. 13B shows the normal view of a contemplated vertical dewatering press 1320.

Figure 14:
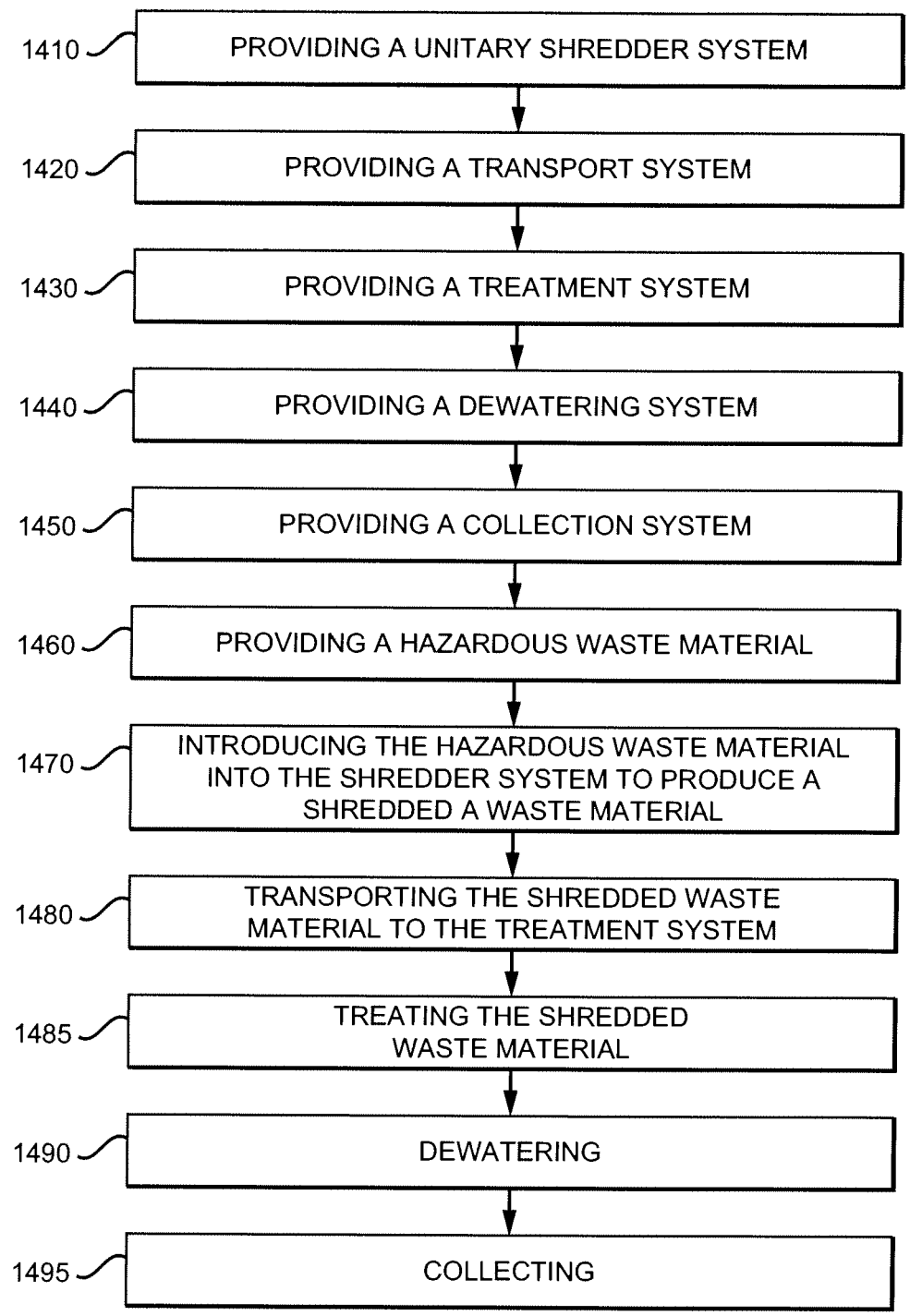
FIG. 14 shows a contemplated method of sanitizing hazardous waste material that includes: a) providing a unitary shredder system 1410, b) providing a transport system, a pre-treatment system or a combination thereof, comprising a reciprocating operation system 1420, c) providing a treatment system 1430, d) providing a dewatering system, a desolutionizing system or a combination thereof 1440, e) providing a collection system for disposal 1450, f) providing a hazardous waste material 1460, g) introducing the hazardous waste material into the shredder system to produce a shredded waste material 1470, h) transporting the shredded waste material to the treatment system utilizing the transport system, the pre-treatment system or a combination thereof, wherein the treatment system, the pre-treatment system or the combination thereof comprises a reciprocating operation system 1480, i) treating the shredded waste material to produce a shredded treated material 1485, j) dewatering or desolutionizing the shredded treated material 1490, and k) collecting the shredded treated material in the collection system 1495.

Methods of sanitizing hazardous waste material 1400 are described, shown in FIG. 14 and include: a) providing a unitary shredder system 1410, b) providing a transport system, a pre-treatment system or a combination thereof, comprising a reciprocating operation system 1420, c) providing a treatment system 1430, d) providing a dewatering system, a desolutionizing system or a combination thereof 1440, e) providing a collection system for disposal 1450, f) providing a hazardous waste material 1460, g) introducing the hazardous waste material into the shredder system to produce a shredded waste material 1470, h) transporting the shredded waste material to the treatment system utilizing the transport system, the pre-treatment system or a combination thereof, wherein the treatment system, the pre-treatment system or the combination thereof comprises a reciprocating operation system 1480, i) treating the shredded waste material to produce a shredded treated material 1485, j) dewatering or desolutionizing the shredded treated material 1490, and k) collecting the shredded treated material in the collection system 1495.

All pre-treatment components, treatment components, chemicals, water and combinations thereof are recyclable and recycled through contemplated processes and devices. This functionality further improves the "green friendly" or environmental friendliness of a contemplated device and process.

Contemplated hazardous waste sanitation and removal device systems may be placed at any location at or near the facility that is producing the waste. As mentioned earlier, this system is unique is that it is relatively portable, while at the same time being very powerful in its ability to convert hazardous wastes to relatively benign components. Contemplated systems may be placed at or near the trash area or loading dock for the facility. Contemplated systems may also be placed near a waste chute, such that wastes are disposed of in the facility, fall directly into the shredder system hopper and are subsequently processed.

One example of such a system may be that the different rooms of the facility contain a locked box where hazardous wastes, such as sharps or gloves, are placed after use. The locked box contains a small bag that collects wastes. When the bag is full, the bottom of the box is triggered to open, releasing the bag into the chute. The bag falls into the shredder system hopper, where it is either immediately processed or held until the shredder system hopper is full. In another example, hazardous wastes are collected throughout the day and manually carried to the shredder system hopper or another containment area. Then, during the day or when the containment area is full, the wastes are shredded and processed.

In some contemplated systems, it may be necessary to add some front end or back end sorting system in order to segregate certain materials, such as radioactive materials. As with many, if not all, of the processes and systems disclosed herein, the central control system, the at least one monitoring system or the combination thereof will determine which materials need to be sorted, where in the process is it most efficient to sort the materials and where to segregate and further treat those materials.

Thus, specific embodiments and applications of a hazardous waste sanitation and removal device and system, along with methods of use and applications thereof have been disclosed. It should be apparent, however, to those skilled in the art that many more modifications besides those already described are possible without departing from the inventive concepts herein. The inventive subject matter, therefore, is not to be restricted except in the spirit of the disclosure herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

We claim:

1. A hazardous waste sanitation and removal device, comprising:
   a central control system, at least one monitoring system or a combination thereof that actively monitors the sanitation and removal device,
   a unitary dry-shredding shredder system, wherein the shredder system produces a shredded waste material,
   a transport system operatively and directly coupled to the dry-shredding shredder system, consisting of a reciprocating operation system and a pipe system, wherein the reciprocating operation system comprises an inlet, an outlet, a high volume vacuum system and a compressed air system,
   a treatment system, comprising an inlet and an outlet, wherein the inlet of the treatment system is operatively and directly connected to the outlet of the reciprocating operation system, wherein the central control system, at least one monitoring system or a combination thereof monitors, tests or otherwise checks or tests the shredded waste material to determine the level of hazardous contaminants, wherein if the level of contaminants exceeds a pre-determined level, a dosage of at least one treatment component is introduced to the treatment system, and wherein the transport system is separate from the treatment system, in that shredded waste material is not treated in the transport system,
   the reciprocating operation system, wherein the reciprocating operation system is operatively located between the dry-shredding shredder system and the treatment system and moves hazardous wastes from the dry shredder to the treatment system,
   a dewatering system, a desolutionizing system or a combination thereof, wherein the dewatering system is operatively connected to the outlet of the treatment system, and
   a collection system for disposal.

2. The hazardous waste sanitation and removal device of claim 1, wherein the treatment system comprises a batch system, a continuous system or a combination thereof.

3. The hazardous waste sanitation and removal device of claim 1, wherein the treatment system utilizes at least one liquid treatment component, at least one gaseous treatment component, at least one solid treatment component or a combination thereof.

4. The hazardous waste sanitation and removal device of claim 3, wherein the at least one liquid treatment component comprises at least one oxygen-containing chemical compound.

5. The hazardous waste sanitation and removal device of claim 4, wherein the at least one oxygen-containing chemical compound comprises chlorine dioxide, hydrogen peroxide, water, deionized water or a combination thereof.

6. The hazardous waste sanitation and removal device of claim 3, wherein the at least one gaseous treatment component comprises ozone, chlorine dioxide or a combination thereof.

7. The hazardous waste sanitation and removal device of claim 1, wherein the monitoring system measures time, volume, contaminant concentration, chemical concentration or a combination thereof.

* * * * *